United States Patent [19]

Takahashi et al.

[11] Patent Number: 4,869,909
[45] Date of Patent: Sep. 26, 1989

[54] PROCESS FOR PRODUCING A MEDICAL VINYL CHLORIDE RESIN MATERIAL

[75] Inventors: Hideo Takahashi; Kouichi Iwata, both of Hyogo, Japan

[73] Assignee: Sumitomo Electric Industries, Osaka, Japan

[21] Appl. No.: 138,115

[22] Filed: Dec. 28, 1987

[30] Foreign Application Priority Data

Dec. 25, 1986 [JP] Japan .............................. 61-312554
Jan. 12, 1987 [JP] Japan .............................. 62-5728
Jan. 12, 1987 [JP] Japan .............................. 62-5729
Oct. 19, 1987 [JP] Japan .............................. 62-264585

[51] Int. Cl.$^4$ .............................................. A61K 9/14
[52] U.S. Cl. .................................. 424/486; 424/484; 427/2; 427/384; 523/122
[58] Field of Search ................ 424/486, 484; 523/122; 427/2, 384

[56] References Cited

U.S. PATENT DOCUMENTS 4,555,398 11/1985 Oda ..................................... 424/19

Primary Examiner—Thurman K. Page
Attorney, Agent, or Firm—Sughrue, Mion, Zinn, Macpeak & Seas

[57] ABSTRACT

A process for producing a medical resin material comprising the steps of (a) adding and dispersing a porous powder containing a pharmaceutical solution in the fine pores thereof to a solution of a polyvinyl chloride resin which is prepared by uniformly dissolving a polyvinyl chloride resin into an organic solvent, thereby preparing a uniform mixed solution; (b) shaping by utilizing the flow property of the mixed solution; and (c) solidifying the shaped mixed solution by evaporizing to remove the organic solvent.

9 Claims, 1 Drawing Sheet

PROCESS FOR PRODUCING A MEDICAL VINYL CHLORIDE RESIN MATERIAL

FIELD OF THE INVENTION

The present invention relates to a process for producing a medical material made of a vinyl chloride resin provided with a slow releasing effect of pharmaceutical substances over a long period of time. More specifically, the present invention relates to a process for producing a medical material made of a vinyl chloride resin capable of providing slow chemical releasability in a simple production process with neither heat decomposition nor heat degradation of the pharmaceutical substances employed.

BACKGROUND OF THE INVENTION

Polyvinyl chloride resins (hereinafter referred to as "PVC resins") are excellent in terms of strength, processability, and living body safety and are economical advantageous. Thus, PVC resins have generally been used in the medical field such as for infusion bags, artificial dialysis circuits, catheters, etc.

It is sometime necessary, depending on the use, to combine PVC resin with other chemicals so as to provide the PVC resins with pharmaceutical effects which are not inherent to the PVC resins. Various methods have been employed therefor.

For example, Japanese Patent Application (OPI) No. 65009/84 and U.S. Pat. No. 4,555,398 disclose a method of adding and kneading a vasodiolator to a PVC resin or similar resin thereby obtaining a slow releasing effect for the vasodiolator. Although the method is simple and excellent from an economical point of view, it is difficult to control the slow releasing rate of the pharmaceutical substance since the vasodiolator itself is merely added and dispersed In this case, the pharmaceutical substance is disadvantageously released in a relatively short period of time.

Japanese Patent Application (OPI) No. 14358/82 discloses a method of coating a resin comprising a hydrophobic polymer graft-complymerizing thereon a hydrophilic monomer to the surface of PVC resins and ionically bonding the coating polymer with heparin as an anticoagulant. Although the slow releasing property of heparin from the composition obtained by this method is satisfactory, the steps of grafting and ionically bonding are complicated and thus is economically disadvantageous.

Japanese Patent Application (OPI) No. 45537/87 discloses a method of adding and dispersing porous power, which is previously impregnated with a phaumaceutical solution into fine pores thereof, to a matrix resin thereby providing the slow releasing property of the pharmaceutical substances. Although this method is simple in production step and excellent in slow releasability of the pharmaceutical substance, if a PVC resin is used as the matrix resin, there is a problem in that this method can not be applied to thermally instable substances, for example, heparin or urokinase since the processing temperature for the PVC resin is as high as from 150 to 190° C. in the usual melt kneading or paste processing step.

Although a solution method of dissolving PVC resins in an organic solvent may be used as a PVC resin processing method which needs no heating, the polymerization degree of the PVC resin used is limited in view of its solubility. This results in problems, i.e., the strength and the impurity leaching property as a medical material are insufficient. In addition, it cannot be used in extrusion molding since the material drips from a nozzle because of the low viscosity of the solution containing the organic solvent

SUMMARY OF THE INVENTION

An object of the present invention is to provide a process for producing a medical vinyl chloride resin material having a slow releasing effect of pharmaceutical substances over a long period of time.

Another object of the present invention is to provide a process for producing a medical vinyl chloride resin material in a simple production process with neither heat decomposition nor heat degradation of the pharmaceutical substances.

Other objects of the present invention will be apparent from the following description.

As a result of the extensive studies by the present inventors, the above objects of the present invention are attained by a process for producing a medical resin material comprising the steps of (a) adding and dispersing a porous powder containing a pharmaceutical solution in the fine pores thereof to a solution of a polyvinyl chloride resin which is prepared by uniformly dissolving a polyvinyl chloride resin into an organic solvent, thereby preparing a uniform mixed solution; (b) shaping by utilizing the flow property of the mixed solution; and (c) solidifying the shaped mixed solution by evaporizing to remove the organic solvent.

DETAILED DESCRIPTION OF THE INVENTION

Figure 1:
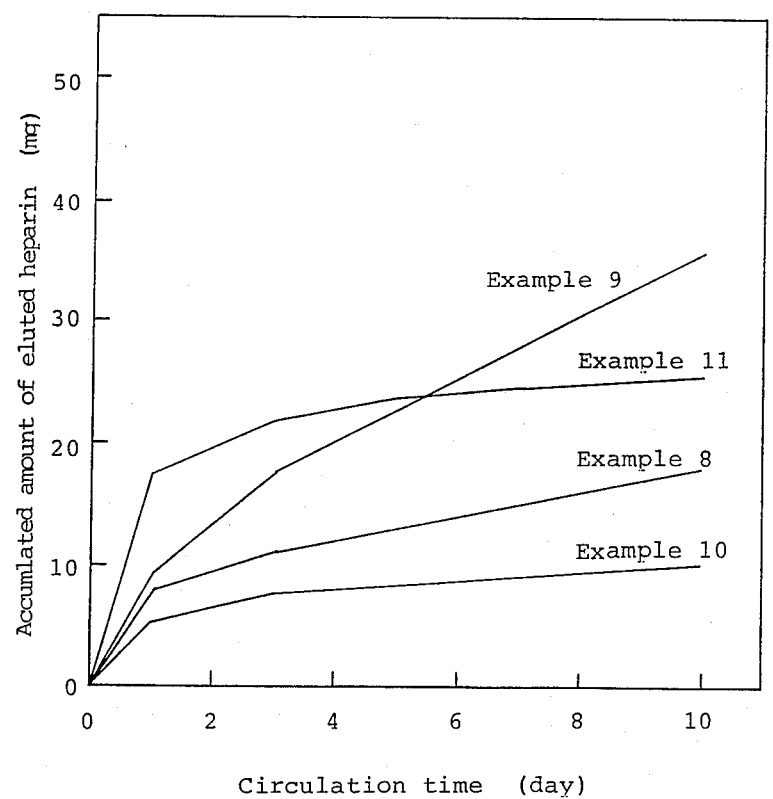
FIG. 1 is a graph showing the relationship between the accumulated amount of eluted heparin from the tubes of the medical vinyl chloride resin material according to the present invention prepared in Examples 8 to 11, and the circulation time of physiological saline.

In the present invention, thermal fusibility of the PVC resin is not utilized for disintegrating the entangled molecular chains of a PVC resin for uniformly adding and dispersing a porous powder impregnated with a pharmaceutical substance. Rather, in the present invention, dissolution with an organic solvent is used. While the solvent process has been used only for PVC resins having a low polymerization degree, it has been found in the present invention that the process can be applied to the dissolution of a PVC resin at any desired polymerization degree and to the uniform dispersion of additives to the PVC resin.

In the process according to the present invention, since the flow property of the solution is utilized for shaping the medical vinyl chloride resin material, no high temperature heating is necessary. In addition, the organic solvent can be evaporated off by using known methods, such as drying under a reduced pressure, whereby a slow releasing property of pharmaceutical substance can be provided to the PVC resin in a simple production method at a relatively low temperature with no thermal degradation of the pharmaceutical substances.

In the production process for the medical vinyl chloride resin material according to the present invention, preferred embodiments for the shaping method utilizing the flow property of the mixed solution can include, for example, the followings:

(i) A coating layer is formed on a substrate by utilizing the flow property of the mixed solution, then the coating layer is solidified by evaporating to remove the organic solvent and the coating layer is fixed on the substrate.

(ii) The mixed solution is cast on a releasable substrate by utilizing the flow property of the mixed solution, the cast product is solidified by evaporating to remove the organic solvent, and then the solidified (iii) The organic solvent is evaporated to remove under stirring until the mixed solution is gelified to such a state that the mixed solution no longer has the flow property, then the gel-like composition is shaped by extrusion molding at a temperature lower than the boiling point of the organic solvent, and then the organic solvent is completely evaporized and removed.

In view of the slow releasability of the pharmaceutical substance, it is preferred for conducting shaping and solidification that two or more kinds of mixed solutions having different pharmaceutical concentrations are successively employed thereby forming two or more coating layers, provided that the pharmaceutical concentration of the inner layer of the solidified layers is higher, more preferably 2 times or higher, than that of the layer on the side where the pharmaceutical substance is eluted.

Examples of the PVC resin used as the matrix resin in the present invention include commercially available PVC type resins, such as straight chain PVC resins obtained by a suspension polymerization or emulsification polymerization process, or other PVC copolymers. The polymerization degree of the PVC resins is adequately selected depending on the application uses. Those having a polymerization degree of from 1,000 to 1,500 are used for general medical application uses, and those having a polymerization degree of from 2,300 to 2,800 are used for tubes for use in peristal pumps They may be in any form such as pellet, powder, flake, etc., and fine powder, particularly fine powder having an average grain size of 0.1 mm or less, is preferred in view of a high dissolving rate in the organic solvent These PVC resins can be used in the present invention after removing the impurities contained therein which are deleterious to living body by conventional methods for purification, such as by washing with metanol.

The organic solvent used in the present invention may be any one of those capable of dissolving PVC resins, and examples thereof include tetrahydrofuran and cyclohexanone.

Examples of the pharmaceutical substance used in the present invention include heparin and its salts as an anticoagulant, urokinase as a thrombus remover, adreamycine as an anti-tumour agent, or a hormonic agent, an anti-cancelogenic agent, an antiinflammatory agent, an antimicrobacterial agent, etc.

In the present invention, the pharmaceutical substance is preferably used in the form of solution, and such a state of the pharmaceutical substance (i.e., the form of solution) is preferably maintained after finally removing the organic solvent for the PVC resin When the pharmaceutical substance used is in a solid state, it may be dissolved in a suitable solvent which is preferably sparingly volatile For example, glycerine which has a high boiling point of 290° C. and is highly safe for the living body is preferably used as the solvent for a heparin salt in the form of powder The porous powder used in the present invention functions as the adsorbing carrier for the pharmaceutical solution, and any porous powder may be used which is not soluble in the pharmaceutical solution and the organic solvent for the PVC resin and has fine pores open to the surface of the powder. Examples thereof include silica gel powder, activated carbon, and synthetic zeolite. The preferred grain size of the porous powder is in the range of from 0.1 to 40 $\mu$m, and more preferably from 1 to 10 $\mu$m. The preferred pore volume of the porous powder is 0.3 ml/g or more for synthetic zeolite, and more preferably 0.6 ml/g or more for silica gel powder.

The fine pores of the porous powder can be impregnated with the pharmaceutical solution, by admixing a porous powder with a mixed solvent comprising solvent A as a good solvent for the pharmaceutical substance and solvent B compatible with solvent A and having a higher boiling point than that of solvent A, thereby preparing a slurry or suspension, and then removing solvent A from the mixture by way of during under a reduced pressure.

The amount of the pharmaceutical solution is preferably a total pore volume of the porous powder or less.

The PVC resin can uniformly be dissolved in an organic solvent at room temperature by using a conventional mixer, dissolver, or stirrer. The amount of the organic solvent is preferably from 600 to 1,000 parts by weight per 100 parts by weight of the PVC resin (the parts hereinafter means parts by weight). If it is less than 600 parts, the PVC resin does not dissolve uniformly and the flow property is reduced. If it is greater than 1,000 parts, although the solubility and the flow property are satisfactory, a great amount of the organic solvent has to be removed by evaporation after shaping, which is undesirable from an economical point of view.

The porous powder impregnated with the pharmaceutical solution can be added and dispersed to the PVC resin solution alone or in combination with additives, such as a plasticizer or a stabilizer, which are generally added to PVC resins, by using a conventional mixer, stirrer, dissolver, etc. Further, for improving the uniform dispersibility, it is preferred to previously knead pharmaceutical solution-impregnated porous powder, plasticizer, etc on a three-roll or inking mill, and then adding them to the PVC resin solution.

The plasticizer and the stabilizer used in the present invention should have a low toxity. Preferred examples of the platicizer include di-2-ethylhexyl phthalate and trioctyl trimellitate. Preferred examples of the stabilizer include a Ca-Zn type stabilizer which is conventionally used for PVC resins as a non-toxic stabilizer.

The organic solvent for the PVC resin should not be compatible with the pharmaceutical solution If it is compatible, the pharmaceutical solution impregnated into the fine pores of the porous powder leaches out, and this degrades the slow releasing property of the pharmaceutical substance of the material In addition, since the organic solvent for the PVC resin is finally evaporated, it should have a boiling point lower than that of the pharmaceutical solution.

The amount of the porous powder impregnated with the pharmaceutical solution is preferably in the range of from 20 to 150 parts, more preferably from 30 to 80 parts, per 100 parts of the PVC resin.

The thus obtained mixed solution of PVC resin has a good flow property at room temperature and can be shaped easily by various methods. For example, a coating layer can be formed on a substrate by a usual coating method or dipping method. Further, shaping can be carried out by casting on a releasable substrate.

The substrate for use in the shaping method can optionally be selected from usual commercially available plastic, elastomer, rubber, metal, ceramic, and glass materials which can satisfy the strength, corrosion resistance, and safety demands required for medical materials and the form thereof is not limited.

Conventional surface treatments, such as primer coating, can be applied as required to the substrate for fixing the PVC resin coating layer thereon in order to increase the adhesive force between the PVC coating layer and the substrate.

The releasable substrate can property be selected depending on the desired shape of the PVC resin material. For instance, a medical PVC resin sheet can be obtained easily by casting the mixed solution on a sheet-like material, such as made of polyethylene terephthalate, standing still for drying and then stripping from the substrate. A medical PVC resin tubular material can be prepared easily, for example, by coating the inner surface of a silicon rubber tube, etc. with the mixed solution, evaporating the organic solvent by drying, and then withdrawing the coating layer on the inner surface from the silicone rubber tube.

On the other hand, since the mixed solution of PVC resin in the present invention has a high flow property at room temperature and drips from a nozzle or die, it can not be used as it is for the extrusion molding It has been found in the present invention that when the organic solvent is removed by evaporation under stirring until the mixed solution forms a gel-like product no longer having the flow property, the gel-like product can be provided with a predetermined shape by extrusion molding with no dripping. For evaporating to remove the organic solvent under stirring, a conventional mixer, dissolver or kneader can be used. The amount of the organic solvent in the gel-like product is preferably from 100 to 400 parts per 100 parts of the PVC resin. If the amount of the organic solvent is less than 100 parts, the gel-like products after extrusion molding have many crazings and can not have practical strength. If the amount of the organic solvent is more than 400 parts, the products discharged from the nozzle or the die upon extrusion molding tend to drip and it is difficult to maintain a predetermined shape.

The gel-like products can be applied with extrusion molding into a desired shape, such as a tubular or sheet-like shape, by using a conventional screw type or plunger type extruder at a temperature lower than the boiling point of the organic solvent. If the temperature in the extruder is higher than the boiling point of the organic solvent, degradation in the surface smoothness and unevenness in the shape will occur due to blister and spitting of the resulting extrusion molding product Therefore, the temperature in the extruder should be lower than the boiling point of the organic solvent.

The organic solvent in the mixed solution after the shaping obtained as described above or the organic solvent remaining in the extrusion molding product can easily be removed by evaporation at a relatively low temperature by the usual drying treatment such as drying under a reduced pressure. For instance, in the case of using tetrahydrofuran having a boiling point of 66° C. as the organic solvent, the organic solvent can be removed by drying at 50° C. under a reduced pressure, by which medical vinyl chloride resin material can be obtained without causing thermal degradation of urokinase, heparin, etc. which are thermally unstable.

The thus obtained medical PVC resin material has micro communication channels in its inside formed upon evaporation of the organic solvent and, when in contact with a solution, such as blood, the pharmaceutical solution impregnated in the fine pores of the porous powder is gradually eluted through the communication channels to develop a slow releasing effect for a long period of time.

As apparent from the foregoing features of the present invention, it is necessary that the organic solvent for the PVC resin is not compatible to the pharmaceutical solution and has a lower boiling point than the pharmaceutical solution. Further, the porous powder should not be soluble to the organic solvent for the PVC resin and the pharmaceutical solution Further, the substrate optionally used upon shaping should be free from corrosion or degradation due to the pharmaceutical solution.

As an example of a combination for satisfying such conditions, it has been found in the present invention that the organic solvent for PVC resin is preferably tetrahydrofuran, and the porous powder is preferably silica gel powder impregnated in the fine pores thereof with a glycerin solution of heparin sodium salt or urokinase. Further, in the case of fixing the PVC resin coating layer made of such material on the substrate, it has been found that a PVC resin is preferably used as the substrate.

The present invention is illustrated in more detail referring to the following examples, but it should be noted that the invention is no way limited only thereto. Unless indicated otherwise, all percents, ratios, and parts are by weight.

EXAMPLE 1

Powder of heparin sodium salt as an anticoagulant, water (boiling point: 100° C.), and glycerin (boiling point: 290° C.) were mixed together in amounts of 10 g, 500 g, and 40 g, respectively, to prepare a uniform solution 25 g of silica gel (average grain size of 3 $\mu$m and pore volume of 1.6 cc/g) was added and dispersed in the solution to obtain a liquid suspension. The liquid suspension was vacuum-dried at 60° C. and 30 mmHg for 8 hours to remove the water content and thereby to obtain a solid cake. The product was slightly ground in a mortar to obtain a fine power with no stickiness and having a favorable powder flowing property.

A mixture prepared by uniformly mixing the thus obtained solution impregnated silica, di-2-ethylhexyl phthalate as a plasticizer, and a Ca-Zn type stabilizer as a stabilizer was added and dispersed into a solution containing 100 parts of PVC resin (average polymerization degree of 1,700) in 800 parts of tetrahydrofuran (hereinafter referred to as "THF") to obtain a uniform PVC resin mixed solution.

The resulting mixed solution was applied to the inner surface of a soft PVC resin tube of a 5 mm inner diameter to cast into the PVC resin tube. After air drying, the resulting coated tube was dried under a reduced pressure to remove the THF by evaporation.

The amount proportion of the starting materials was determined so that the composition of the coating layer after drying comprises 60 parts of di-2-ethylhexyl phthalate, 40 parts of the liquid impregnated silica, and 2 parts of the Ca-Zn type stabilizer per 100 parts of the PVC resin. An SEM observation of the cut-out surface of the resulting coated tube determined that a uniform coating layer having an average thickness of 70 $\mu$m was formed and the adhesive force between the soft PVC substrate and the coating layer was favorable.

The resulting coated tube was cut to a 30 cm length, through which physiological saline was circulated at 20 cc/min and the amount of heparin sodium salt which was eluted into the physiological saline was measured by utilizing the coloration reaction between toluidine blue and heparin sodium salt. The results are shown in Table 1 below.

TABLE 1

| Circulation time of physiological saline (hour) | Accumulated amount of eluted heparin (mg) |
|---|---|
| 0.5 | 0.49 |
| 5 | 0.70 |
| 24 | 0.81 |
| 72 | 3.12 |

From the results shown in Table 1, it is apparent that the medical PVC resin material according to the present invention attains a satisfactory slow releasing property of a pharmaceutical substance.

EXAMPLE 2

The inner surface of a soft PVC resin tube of a 3 mm inner diameter and a 4 mm outer diameter was applied with a coating layer using the same procedures as in Example 1 except for using anti-thrombus urokinase instead of heparin sodium salt.

The adhesion force between the coating layer and the substrate tube was satisfactory and neither peeling nor crazing occurred even when the tube was squeezed The resulting tube was cut diametrically to a 5 mm thickness and, after immersing for 24 hours in physiological saline, the diametrically cut surface was placed on a flat fibrin plate, stood still at 37° C. for 24 hours to measure the fibrin dissolving activity of the urokinase depending on the degree of the dissolution of the fibrin membrane around the test specimen. As a result, the fibrin membrane around the test specimen was dissolved in a form of a circle having a 15 mm diameter and the slow releasing property of the urokinase was confirmed.

EXAMPLE 3

The same uniform PVC resin mixed solution as prepared in Example 1 was cast into a 10 cm square stainless steel frame having a 0.6 mm thickness placed on a polyethylene terephthalate sheet. After air drying, dried under vacuum at 50° C. for 8 hours to obtain a smooth PVC resin sheet having a thickness of 0.17 mm. The resulting sheet could easily be separated from the polyethylene terephthalate sheet and had a sufficient strength.

The resulting sheet was cut to a 3 cm square to prepare a test specimen and the anti-thrombus effect of the sheet was evaluated by the Imai-Nose method (as described in J. Biomed. Mater. Res., vol. 6, page 165 (1972). That is, blood of a dog was dropped on the test specimen and stood still at 37° C. for 15 minutes. Then, the weight of blood clot formed on the test specimen was measured. As a result, no blood clot was formed.

After washing the test specimen 5 times each time with 20 cc of distilled water, the same test as above was repeated for 8 times, but the blood clot was not formed and the maintenance of the anti-thrombus effect of the specimen was confirmed.

EXAMPLE 4

The mixed PVC resin solution obtained in Example 1 was cast into a silicone rubber tube of a 4 mm inner diameter and a 600 mm length to coat the inner surface of the tube. Then, after air drying, vacuum drying was conducted at 50° C. for 8 hours to remove the THF in the coating layer by evaporation. Next, while the coating layer was extracted by gripping the end thereof, the layer could be withdrawn easily to obtain a PVC resin tube having an outer diameter of 4 mm and an inner diameter of 3.7 mm having a satisfactory surface property and strength.

The resulting tube was cut to a 30 cm length through which physiological saline was circulated at 20 cc/min and an amount of heparin sodium salt eluted into the physiological saline was measured by utilizing the coloration reaction between toluidine blue and heparin sodium salt. The results are shown in Table 2 below.

TABLE 2

| Circulation time of physiological saline (hour) | Accumulated amount of eluted heparin (mg) |
|---|---|
| 0.5 | 0.39 |
| 5 | 0.63 |
| 24 | 1.70 |
| 72 | 3.04 |

From the results shown in Table 2, it is apparent that the medical PVC resin material according to the present invention attains a satisfactory slow releasing property of a pharmaceutical substance.

EXAMPLE 5

A tube having an outer diameter of 4 mm and an inner diameter of 3.7 mm was obtained by the same procedures as in Example 4 except for using anti-thrombus urokinase instead of heparin sodium salt. The resulting tube was evaluated in the same manner as in Example 2. As a result, the fibrin membrane was dissolved in the form of a circle having a diameter of mm around the test specimen to confirm the slow releasing effect of the urokinase.

EXAMPLE 6

The uniform PVC resin mixed solution obtained in Example 1 was stirred in a dissolver at room temperature for 30 minutes to evaporate the THF to thereby obtain a gel-like product having no flow property. The gel-like product had a composition comprises 60 parts of di-2ethylhexyl phthalate, 40 parts of the liquid-impregnated silica, 2 parts of the Ca-Zn type stabilizer, and 140 parts of THF per 100 parts of the PVC resin.

The gel-like product was supplied to a screw type extruder and a tube having an inner diameter of 5 mm and an outer diameter of 7 mm was extruded at room temperature. The extrudability was satisfactory and the resulting tube had a satisfactory surface property although it was white and not transparent.

After completely evaporating to remove the organic solvent from the resulting tube by carrying out vacuum drying at 50° C., the tube was cut to a 30 cm length, through which physiological saline was circulated at 20 cc/min, and the amount of heparin sodium salt eluted into the physiological saline was measured by utilizing the coloration reaction between toluidine blue and heparin sodium salt. The results are shown in Table 3 below. Further, the result of the tensile test for the resulting tubes ar shown in Table 4 below.

TABLE 3

| Circulation time of physiological saline (hour) | Accumulated amount of eluted heparin (mg) |
| --- | --- |
| 0.5 | 1.26 |
| 5 | 3.72 |
| 24 | 4.20 |
| 72 | 6.15 |

From the results shown in Table 3, it is apparent that the medical PVC resin material according to the present invention attains a satisfactory slow releasing property of a pharmaceutical substance.

COMPARATIVE EXAMPLE 1

After admixing 40 parts of porous silica gel impregnated with the glycerin solution of heparin sodium salt used in Example 1, 60 parts of di-2-ethylhexyl phthalate, and 2 parts of the Ca-Zn type stabilizer used in Example 1 to 100 parts of a commercial PVC resin for extrusion molding having an average polymerization degree of 720, a tube having a 7 mm outer diameter and a 5 mm inner diameter was extrusion molded at 160° C. The resulting tube turned brown due to the thermal degradation of heparin sodium salt and elution of heparin sodium salt from the tube was not observed. The result of the tensile test for this product is shown in Table 4 below.

TABLE 4

| Specimen | Elongation at break under tension (%) | Strength at break under tension (kg/cm$^2$) |
| --- | --- | --- |
| Example 6 | 225 | 148 |
| Comparative Example 1 | 86 | 176 |

(note) Distance of chuks: 50 mm
Load rate: 50 mm/min

From the results shown in Table 7, it is apparent that the medical PVC resin material according to the present ivention attains a satisfactory strength.

EXAMPLE 7

A tube having an inner diameter of 5 mm and an outer diameter of 7 mm was extruded in the same procedures as in Example 6 except for using anti-thrombus urokinase instead of heparin sodium salt. The resulting tube had a satisfactory surface property although it was white and not transparent. Thereafter, the organic solvent remained in the tube was removed in the same manner as in Example 6.

The resulting tube was evaluated in the same manner as in Example 2. As a result, the fibrin membrane was dissolved in a shape of circle having a diameter of 21 mm around the test specimen and the slow releasing property for the urokinase was confirmed.

EXAMPLE 8

After preparing a uniformly mixed solution by mixing 30 g of heparin sodium salt powder as anticoagulant, 70 g of glycerin, and 500 g of water, 70 g of porous silica gel (average grain size of 3 μm, pore volume of 1.6 cc/g) was admixed to prepare a liquid suspension. Then, it was dried under a reduced pressure at 30 mmHg and 60° C. for 8 hours to remove the water content and to obtain a solid cake. The product was coarsely pulverized in a coffee mill grinder and, after admixing trioctyl trimellitate as a plasticizer, kneaded on a 3-roll kneader to obtain a paste-like product in which the porous silica gel containing the pharmaceutical solution was uniformly dispersed. The weight ratio of the pharmaceutical solution-containing porous silica gel and the plasticizer was 4/7.

200 parts of the paste-like product was added and dispersed into a PVC resin solution in which 100 parts of a PVC resin (average polymerization degree: 1,700, average grain size: 0.8 μm) was uniformly dissolved in 800 parts of THF to prepare mixed solution (A).

After preparing a uniformly mixed solution by mixing 20 g of heparin sodium salt powder as anticoagulant, 80 g of glycerin, and 500 g of water, 90 g of porous silica gel (average grain size of 3 μm, pore volume of 1.6 cc/g) was admixed to prepare a liquid suspension. Then, it was dried and coarsely pulverized in the same manner as in the preparation of mixed solution (A). After admixing trioctyl trimellitate as a plasticizer, kneaded on a 3-roll kneader to obtain a paste-like product in which the porous silica gel containing the pharmaceutical solution was uniformly dispersed. The weight ratio of the pharmaceutical solution-containing porous silica gel and the plasticizer was 4/7.

110 parts of the paste-like product was added and dispersed into a PVC resin solution used in the preparation of mixed solution (A) to prepare mixed solution (B).

The amount of the heparin sodium salt in the composition without THF was 4.3% by weight for solution (A) and 2.0% by weight for solution (B).

Solution (A) was cast into a soft PVC resin tube having a 4 mm inner diameter to apply coating to the inner surface of the PVC resin tube. After air drying, vacuum drying at 50° C. was carried out to remove the THF by evaporization to form a coating layer of about 100 μm thickness. Solution (B) was further cast and the coating layer was formed on the thus-formed coating layer in the same manner to prepare a PVC resin tube having a total coating thickness of about 200 μm.

EXAMPLE 9

Using a silicone rubber tube having a 3 mm outer diameter wherein the immersion side was closed as a core material, and using mixed solutions (A) and (B) prepared in Example 8, dipping and drying were carried out repeatedly in the order of solutions (B), (B), (A), and (A) to form a coating layer having a total coating thickness of 400 μm. When the coating product was slightly squeezed and the end of the silicone rubber tube as the core material was pulled, the silicone rubber tube could be withdrawn easily to obtain a PVC resin tube having a 3.8 mm outer diameter and a 3.0 mm inner diameter and having satisfactory surface property and sufficient strength.

EXAMPLE 10

A PVC resin tube was prepared in the same manner as in Example 8 except that two layers each using mixed solution (B) were provided instead of the coating layers in Example 8.

EXAMPLE 11

A PVC resin tube was prepared in the same manner as in Example 8 except that two layers each using mixed solution (A) were provided instead of the coating layers in Example 8.

The PVC resin tubes obtained in Examples 8 to 11 were cut to 20 cm lengths through which physiological saline was circulated at 20 cc/min and the accumulated amount of the eluted heparin sodium salt was measured by utilizing the coloration reaction between toluidine blue and heparin sodium salt. The results obtained are shown in Table 5 below and FIG. 1.

TABLE 5

| | Accumulated amount of eluted heparin (mg) | | | | |
|---|---|---|---|---|---|
| | Circulation time (day) | | | | |
| Example | 1 | 3 | 5 | 7 | 10 |
| 8 | 7.7 | 10.9 | 12.8 | 14.9 | 17.8 |
| 9 | 9.3 | 17.5 | 22.7 | 27.8 | 35.6 |
| 10 | 5.0 | 7.5 | 8.4 | 9.1 | 10.0 |
| 11 | 17.3 | 21.8 | 23.7 | 24.6 | 25.3 |

As shown in Table 5 and FIG. 1, by providing a layer a higher heparin concentration than that at the surface layer on the elution side, the slow releasing property of heparin can be maintained for a longer period of time as compared with the case of merely disposing layers of an identical composition.

For the portions where the elution of the pharmaceutical solution from the surface is not desired, it is possible to interrupt the elution of the pharmaceutical solution by applying a PVC resin coating not containing the pharmaceutical solution on such a portion.

As described above, by the process for producing a medical vinyl chloride resin material according to the present invention, it is possible to provide a PVC resin with slow releasing property in a simple manner without degrading the pharmaceutical substance by heat, even if the pharmaceutical substance is relatively heat sensitive.

Namely, the elution rate of the pharmaceutical substance is controlled by using the porous powder; the heat degradation of the pharmaceutical substance is avoided by dispersing the pharmaceutical solution in the PVC resin solution; and the excellent slow releasing property is attained since the pharmaceutical substance is in the form of solution in the final product, i.e., the pharmaceutical substance can easily migrate in the material in comparison to the case where the substance is in a solid form.

While the invention has been described in detail and with reference to specific embodiments thereof, it will be apparent to one skilled in the art that various changes and modifications can be made therein without departing from the spirit and scope thereof.

What is claimed is:

1. A process for producing a medical resin material comprising the steps of (a) adding and dispersing a porous powder containing a pharmaceutical solution in the fine pores thereof to a solution of a polyvinyl chloride resin which is prepared by uniformly dissolving a polyvinyl chloride resin having a polymerization degree of from 1,000 to 2,800 into an organic solvent, said pharmaceutical solution being insoluble or sparingly soluble in said organic solvent, thereby preparing a uniform mixed solution; (b) shaping by utilizing the flow property of said mixed solution; and (c) solidifying said shaped mixed solution by evaporation to remove said organic solvent.

2. A process for producing a medical resin material as claimed in claim 1, wherein a coating layer is formed on a substrate by utilizing the flow property of said mixed solution, then said coating layer is solidified by evaporation to remove the organic solvent and said coating layer is fixed on said substrate.

3. A process for producing a medical resin material as claimed in claim 1, wherein said mixed solution is cast on a releasable substrate by utilizing the flow property of said mixed solution, said cast product is solidified by evaporation to remove said organic solvent, and then said solidified product is released from said substrate.

4. A process for producing a medical resin material as claimed in claim 1, wherein said organic solvent is evaporized to remove under stirring until said mixed solution is gelified to such a state that said mixed solution no longer has the flow property, then said gel-like composition is shaped by extrusion molding at a temperature lower than the boiling point of said organic solvent, and then said organic solvent is completely evaporated and removed.

5. A process for producing a medical resin material as claimed in claim 1, wherein two or more of mixed solutions having different pharmaceutical concentrations are shaped and solidified successively thereby forming two or more coating layers, provided that the pharmaceutical concentration of the inner layer of said solidified layers is higher than the pharmaceutical concentration of the layer on the side where the pharmaceutical substance of said pharmaceutical solution is eluted.

6. A process for producing a medical resin material as claimed in claim 1, wherein said organic solvent for dissolving said polyvinyl chloride resin is tetrahydrofuran, and said porous powder is silica gel powder impregnated in the pores thereof with a glycerine solution of heparin sodium salt.

7. A process for producing a medical re in material as claimed in claim 1, wherein said organic solvent for dissolving said polyvinyl chloride resin is tetrahydrofuran, and said porous powder is silica gel powder impregnated in the pores thereof with a glycerine solution of urokinase.

8. A process for producing a medical resin material as claimed in claim 1, wherein said organic solvent is employed in an amount of from 600 to 1,000 parts by weight per 100 parts by weight of said polyvinyl chloride resin.

9. A process for producing a medical resin material as claimed in claim 4, wherein said mixed solution no longer having the flow property contains said organic solvent in an amount of from 100 to 400 parts by weight per 100 parts by weight of said polyvinyl chloride resin.

* * * * *